(12) United States Patent
Lu

(10) Patent No.: US 10,493,045 B2
(45) Date of Patent: Dec. 3, 2019

(54) METHOD FOR TREATING ALCOHOL DEPENDENCE OR ALCOHOL ABUSE

(71) Applicant: Ru-Band Lu, Tainan (TW)

(72) Inventor: Ru-Band Lu, Tainan (TW)

( * ) Notice: Subject to any disclaimer, the term of this patent is extended or adjusted under 35 U.S.C. 154(b) by 0 days.

(21) Appl. No.: 15/835,480

(22) Filed: Dec. 8, 2017

(65) Prior Publication Data

US 2018/0161286 A1   Jun. 14, 2018

Related U.S. Application Data

(60) Provisional application No. 62/433,789, filed on Dec. 14, 2016.

(51) Int. Cl.
| | | |
|---|---|---|
| *A61K 31/13* | (2006.01) | |
| *A61P 29/00* | (2006.01) | |
| *A61P 25/32* | (2006.01) | |
| *A61P 25/18* | (2006.01) | |

(52) U.S. Cl.
CPC ............ *A61K 31/13* (2013.01); *A61P 25/18* (2018.01); *A61P 25/32* (2018.01); *A61P 29/00* (2018.01)

(58) Field of Classification Search
CPC .......... A61K 31/13; A61P 25/18; A61P 25/32; A61P 29/00
See application file for complete search history.

(56) References Cited

U.S. PATENT DOCUMENTS

| 8,461,148 B2 * | 6/2013 | Hollander | A61K 31/13 |
| | | | 514/220 |
| 9,925,179 B2 * | 3/2018 | Lu | A61K 31/00 |
| 2004/0192683 A1 * | 9/2004 | Moormann | A61K 31/185 |
| | | | 514/228.2 |
| 2008/0234257 A1 * | 9/2008 | Gant | C07B 59/00 |
| | | | 514/230.5 |

FOREIGN PATENT DOCUMENTS

EP  2218450 A1 *  8/2010  ............ A61K 31/13

OTHER PUBLICATIONS

Evans et al., "A Pilot Double-Blind Treatment Trial of Memantine for Alcohol Dependence", 2007, Alcohol Clin Exp Res, vol. 31, No. 5, pp. 775-782. (Year: 2007).*
Arias et al., "Memantine for Alcohol Dependence: An Open-label Pilot Study", 2007, Addictive Disorders & Their Treatment, vol. 6, No. 2, pp. 77-83. (Year: 2007).*
Keck et al., "Memantine Efficacy and Safety in Patients With Acute Mania Associated With Bipolar I Disorder: A Pilot Evaluation", 2009, Clinical Neuropharmacology, vol. 32, No. 4, pp. 199-204. (Year: 2009).*
Anand et al., "Early antidepressant effect of memantine during augmentation of lamotrigine inadequate response in bipolar depression: a double-blind, randomized, placebo-controlled trial", 2012, 14(1), pp. 64-70. (Year: 2012).*
Sani et al., "The role of memantine in the treatment of psychiatric disorders other than the dementias", 2012, CNS Drugs, 26(8), pp. 663-690. (Year: 2012).*
Altinbas et al., "Pharmacotherapy Options in Comorbid Bipolar Disorder and Alcohol-Substance Use Disorders", 2013, Klinik Psikofarmakoloji Bülteni-Bulletin of Clinical Psychopharmacology, 23(4), pp. 378-389. (Year: 2013).*
Di Florio et al., "Alcohol misuse in bipolar disorder. A systematic review and meta-analysis of comorbidity rates", 2014, European Psychiatry, 29(3), pp. 117-124. (Year: 2014).*
Simhandl et al., "Prevalence and impact of comorbid alcohol use disorder in bipolar disorder: A prospective follow-up study", 2016, Australian & New Zealand Journal of Psychiatry, 50(4), pp. 345-351. (Year: 2016).*
Lee et al., "Add-OnMennantine Treatment for Bipolar II Disorder Comorbid with Alcohol Dependence: A 12-Week Follow-Up Study", 2018, Alcoholism: Clinical and Experimental Research, 42(6), pp. 1044-1050. (Year: 2018).*

* cited by examiner

*Primary Examiner* — My-Chau T. Tran
(74) *Attorney, Agent, or Firm* — Hannah Tien

(57) ABSTRACT

A method for treating alcohol dependence or alcohol abuse in a subject comprising administering to the subject a composition comprising an effective amount of memantine, wherein the effective amount of memantine is 2-4.7 mg/day. Low dose of memantine having anti-inflammatory and neurotrophic effect is able to reduce alcohol use.

3 Claims, 1 Drawing Sheet

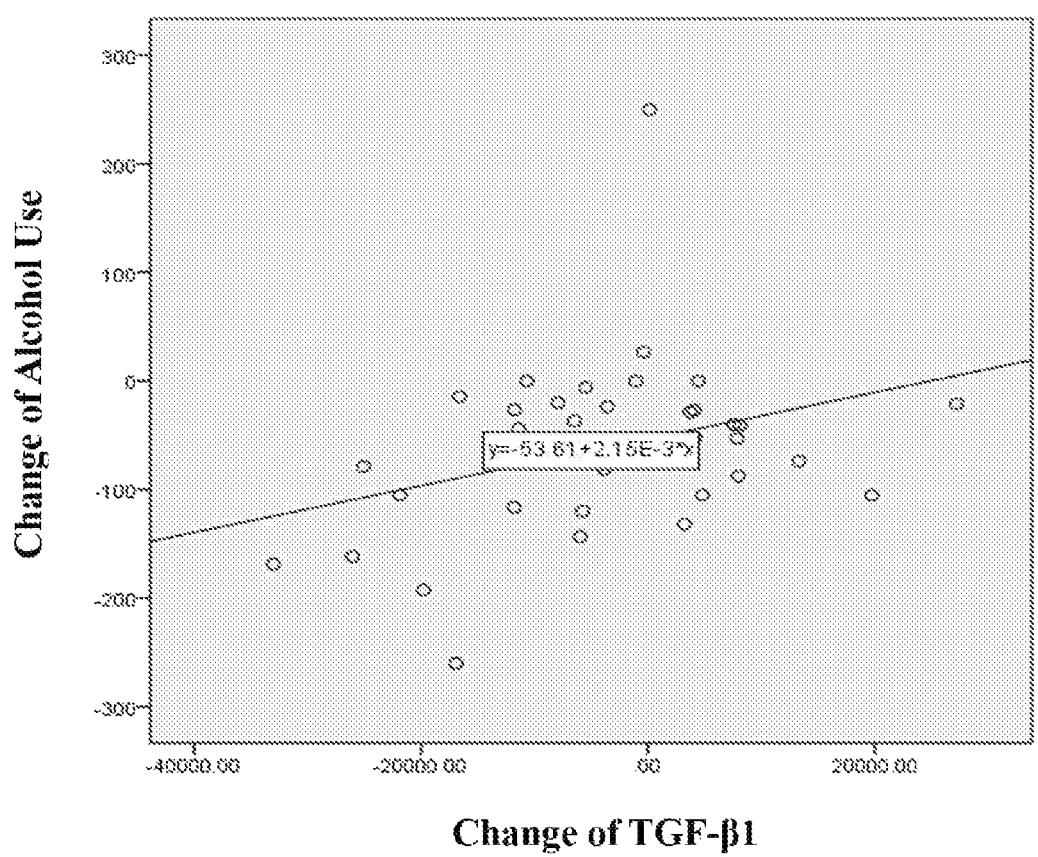

METHOD FOR TREATING ALCOHOL DEPENDENCE OR ALCOHOL ABUSE

The present application claims priority to U.S. Provisional Application No. 62/433,789, filed on Dec. 14, 2016, which is incorporated herein by reference in its entirety.

FIELD OF THE INVENTION

The present invention relates to a method for treating alcohol dependence or alcohol abuse in a subject, comprising administering to the subject a low dose of memantine.

BACKGROUND OF THE INVENTION

Bipolar II disorder (BD-II) is a subtype of bipolar disorder (BD) characterized as "recurrent episodes of depression and hypomania." BD-II is often misdiagnosed because diagnoses are frequently made based on recollections of past hypomania when patients are having symptoms of depression. Therefore, BD-II is often ineffectively treated. Patients with BD-II have a greater risk of suicide, a prolonged clinical course, more mood episodes, more major and minor depressive episodes, and shorter inter-episode intervals, than do patients with bipolar I disorder (BD-I).

Patients with BD frequently have comorbid alcohol use disorders (AUDs), especially patients with BD-II. Irritable and hyperthymic temperaments might contribute to AUDs in BD-II patients. Comorbid AUDs in BD-II patients worsens the clinical presentation with higher rates of mixed episodes, rapid cycling and increased symptom severity. In addition, even in the inter-episode state, BD-II patients comorbid with AUDs performed poorly on verbal, visual, and working memory, psychomotor speed, and attention span tests than did BD-II patients without AUDs and super-normal healthy controls. Both BD and AUDs are neurodegenerative diseases likely to increase toxins and nerve damage in various brain areas; comorbid BD and AUDs might lead to detrimental effects. Alcohol dependence might be categorized into four subtypes: (a) simple, (b) anxiety-depression, (c) mixed (bipolar), and (d) antisocial subtypes with genetic variations in Han Chinese populations (Shan et al., Neuropsychological functions in Han Chinese patients in Taiwan with bipolar II disorder comorbid and not comorbid with alcohol abuse/alcohol dependence disorder. Prog Neuropsychopharmacol Biol Psychiatry, 35:131-136, 2011). Previous clinical experience shows that it is more difficult for BD patients with the mixed subtype to stop drinking than it is for those with the simple and anxiety-depression subtypes.

Memantine is a noncompetitive N-methyl-D-aspartate (NMDA) receptor antagonist. However, an alternative mechanism for memantine has been reported: memantine functions as an anti-inflammatory agent that downregulates the activity of microglia and upregulates astroglia-released neurotrophic factors, which is mechanistically remote from an NMDA receptor (Wu et. Al, Novel neuroprotective mechanisms of memantine: increase in neurotrophic factor release from astroglia and anti-inflammation by preventing microglial activation, Neuropsychopharmacology 34:2344-2357, 2009). Low-dose (0.02 mg/kg) memantine abolishes morphine-induced conditioned-place-preference behavior in rats because of its IL-6-modulating effect on the medial prefrontal cortex and IL-1β-modulating effect on the nucleus accumbens (Chen et al., Low-dose memantine attenuated morphine addictive behavior through its anti-inflammation and neurotrophic effects in rats, Journal of neuroimmune pharmacology: the official journal of the Society on Neuroimmune Pharmacology, 7:444-453, 2012). In addition, add-on memantine in opioid-dependent patients undergoing methadone maintenance treatment not only significantly downregulates plasma tumor necrosis factor-α (TNF-α) levels and upregulates transforming growth factor-β1 (TGF-β1) levels, but also reduces the required methadone dose (Lee et al., Low-dose memantine attenuated methadone dose in opioid-dependent patients: a 12-week double-blind randomized controlled trial, Sic Rep 5:10140, 2015).

SUMMARY OF THE INVENTION

The present invention relates to a method for treating alcohol dependence or alcohol abuse in a subject, comprising administering to the subject a composition comprising an effective amount of memantine, wherein the effective amount of memantine is less than 5 mg/day.

BRIEF DESCRIPTION OF THE DRAWINGS

FIG. 1 shows correlation between changes in alcohol use (unit) and changes in TGF-β1 levels in BD-II patients after a 12-week follow-up.

DETAILED DESCRIPTION OF THE INVENTION

An adequate combination of mood stabilizers plus neuroprotective and anti-inflammatory agents may greatly enhance treatments for BD-II patients with comorbid alcohol dependence. Therefore, the present invention demonstrates that low-dose add-on memantine (less than 5 mg/day) treatment for BD-II patients with comorbid alcohol dependence significantly attenuates clinical severity, reduces alcohol use and plasma cytokine levels, and increases BDNF levels. The present invention also finds a significant correlation between the reduced alcohol use and the reduced plasma transforming growth factor-β1 (TGF-β1) levels.

Because memantine may not only inhibit the overactivity of microglia, but also repair damaged neurons and restore neurogenesis by activating astroglia and upregulating astroglia-released neurotrophic factors, the present invention demonstrates that the neuroprotective and neurotrophic effects of memantine provides benefits to BD-II patients with comorbid alcohol dependence.

As used herein, the term "a" or "an" are employed to describe elements and components of the invention. This is done merely for convenience and to give a general sense of the invention. This description should be read to include one or at least one and the singular also includes the plural unless it is obvious that it is meant otherwise.

As used herein, the term "or" are employed to describe "and/or."

As used herein, the term "patient" refers to a person under or requires health or medical care and/or treatment, wherein the person may be waiting for this care or may be receiving it or may have already received it.

The present invention provides a method for treating alcohol dependence or alcohol abuse in a subject, comprising administering to the subject a composition comprising an effective amount of memantine, wherein the effective amount of memantine is 2-4.7 mg/day.

As used herein, the term "treating" refers to the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relieve the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications.

The term "alcohol dependence" or "alcohol abuse" is defined in the *Diagnostic and Statistical Manual of Mental Disorders, Fourth Edition, Text Revision* (DSM-IV-TR) or the 5th edition of the Diagnostic and Statistical Manual of Mental Disorders (DSM-5) (Diagnostic and Statistical Manual of Mental Disorders, 5th edition, American Psychiatric Publishing, 2013), the entire contents of the definition of "alcohol dependence" and "alcohol abuse" are incorporated herein by reference.

The term "subject" used herein is an animal. In a preferred embodiment, the subject is a mammal. In a more preferred embodiment, the subject is a human.

In one embodiment, the subject suffers from a psychiatric disorder. As used herein, the term "psychiatric disorder" also called a mental disorder, includes mood disorders (e.g., depression of all forms and/or types, bipolar disorder, etc.), schizophrenia, autism spectrum disorder, personality disorders, anxiety, anxiety disorders, substance-related disorders, childhood disorders, dementia, adjustment disorder, delirium, multi-infarct dementia, and Tourette's disorder as described in, e.g., DSM-IV-TR or DSM-5. Typically, such disorders have a complex genetic, biochemical, and/or environmental component. In a preferred embodiment, the psychiatric disorder is induced by neuro-inflammation-related neuronal dysfunction or neurodegeneration.

In another embodiment, the psychiatric disorder comprises bipolar disorder. As used herein, the term "bipolar disorder" includes a mood disorder characterized by alternating periods of extreme moods. A person with bipolar disorder experiences cycling of moods that usually swing from being overly elated or irritable (mania) to sad and hopeless (depression) and then back again, with periods of normal mood in between. Diagnosis of bipolar disorder is described in, e.g., DSM-IV-TR or DSM-5. Bipolar disorders include bipolar I disorder (mania with or without major depression), bipolar II disorder (hypomania with major depression), and cyclothymia. Bipolar disorder is also known as manic depression. In a preferred embodiment, the bipolar disorder comprises bipolar I disorder and bipolar II disorder. In a more preferred embodiment, the bipolar disorder is bipolar II disorder.

Therefore, in one embodiment, the composition of the present invention further comprises a mood stabilizer or antipsychotics. In a preferred embodiment, the antipsychotics comprises valproic acid (VPA). In a more preferred embodiment, the effective amount of VPA is 500-1000 mg/day. Therefore, the effective amount of VPA administered to the subject allows the level of VPA in the plasma of the subject to be between 50 and 100 μg/dl.

In one embodiment, the composition is administered to the subject daily at least for one week. In a preferred embodiment, the composition is administered to the subject daily at least for two weeks. In a preferred embodiment, the composition is administered to the subject daily at least for four weeks. In another embodiment, the composition is administered to the subject daily per week.

As used herein, the term "effective amount" refers to the amount of a pharmaceutical ingredient which substantially induces, promotes or results in a desired therapeutic effect. In an embodiment, the effective amount of memantine is 2-4.7 mg/day. In a preferred embodiment, the effective amount of memantine is 3-4.7 mg/day. In a more preferred embodiment, the effective amount of memantine is 4-4.7 mg/day.

In one embodiment, the effective amount of memantine is sufficient to treat alcohol dependence or alcohol abuse by an anti-inflammatory response and/or a neurotrophic effect. In a preferred embodiment, the anti-inflammatory response and/or the neurotrophic effect comprise reducing cytokine levels and increasing brain-derived neurotrophic factor (BDNF) levels. In a more preferred embodiment, the cytokine comprises tumor necrosis factor-α (TNF-α), C-reactive protein (CRP), transforming growth factor-β1 (TGF-β1), interleukin-8 (IL-8) and IL-10. In another embodiment, the anti-inflammatory response and/or the neurotrophic effect comprise reducing the level of TGF-β1 in the subject.

In various embodiments, the composition is in a form suitable for administration by a route selected from the group consisting of parenteral, transdermal, oral and topical. In a preferred embodiment, the composition is administered by oral route.

The composition of the present invention further comprises a pharmaceutically acceptable carrier. As used herein, the term "pharmaceutically acceptable carrier" refers to a diluent or vehicle which is used to enhance the delivery and/or pharmacokinetic properties of a pharmaceutical ingredient with which it is formulated, but has no therapeutic effect of its own, nor does it induce or cause any undesirable or untoward effect or adverse reaction in the subject. Therefore, the active compounds (memantine) of the present invention can be formulated readily by using pharmaceutically acceptable carriers well known in the art into dosages suitable for oral administration, which is also preferred for the practice of the present invention. Such carriers enable the compounds of the present invention to be formulated in dosage forms such as tablets, lozenges, pills, capsules, liquids, gels, syrups, slurries, suspensions and the like, for oral ingestion by a patient to be treated. These carriers may be selected from sugars, starches, cellulose and its derivatives, malt, gelatin, talc, calcium sulfate, vegetable oils, synthetic oils, polyols, alginic acid, phosphate buffered solutions, emulsifiers, isotonic saline, and pyrogen-free water.

Thus, the effective amount of memantine administered to the subject daily is preferably 4.7 mg. When the composition is formulated in the dosage form of tablets or lozenges, the unitary dose of memantine in each tablet or is preferably 2.3 mg, 2.35 mg, 2.4 mg or 4.7 mg. The above described unitary dose of memantine is designed to meet the daily requirement of 4.7 mg of memantine when one or two tablets/lozenges are administered to the subject each day.

In some embodiments, the composition is in a form suitable for administration by injection. In various embodiments, the composition is a parenteral formulation for administration by a route selected from the group consisting of subcutaneous, intravenous, intramuscular, intradermal, intraperitoneal, intraarterial, intracerebral, intracerebroventricular, intraosseous and intrathecal.

Thus, the present invention demonstrates that the low dose (less than 5 mg) of memantine provides therapeutically benefits to patients with alcohol dependence, specifically to the patients suffering from bipolar disorder. Further, neuro-inflammation-related neuronal dysfunction or neurodegeneration underlies the pathogenesis of bipolar disorder and alcohol dependence. In addition, mood swing may worsen alcohol use. In previous clinical experience, effects on microglial and astroglial cells may have therapeutic effect on neuro-degeneration diseases including mood stabilizing effect on bipolar disorder. As a result, the treatment of low dose of memantine in the present invention is able to significantly affect alcohol use by patients with psychiatric disorders because of anti-inflammatory and neuroprotective effects which stabilize patient's mood.

Examples

The examples below are non-limiting and are merely representative of various aspects and features of the present invention.

Methods:

(a) Patient Selection

The Institutional Review Board for the Protection of Human Subjects at National Cheng Kung University Hospital reviewed and approved the research protocol. All participants were given a detailed description of the study before they signed written informed consent forms.

BD-II patients with comorbid alcohol dependence were recruited from outpatient and inpatient settings in Taiwan. All patients were initially evaluated by an attending psychiatrist and then given a structural interview by a clinical psychologist to determine according to the *Diagnostic and Statistical Manual of Mental Disorders, Fourth Edition, Text Revision* (DSM-IV-TR), and the Chinese version of the Modified Schedule of Affective Disorder and Schizophrenia-Life Time (SADS-L) was used, which had good inter-rater reliability. Patients suffering from major mental illnesses other than BD-II and alcohol dependence and patients who had taken memantine within 1 week before the study began were excluded. Although DSM-IV-TR criteria required a minimum of 4 days of hypomania, the epidemiologic data at the time of the study suggested that a minimum of 2 days of hypomania also met the criteria of BD-II for community samples; therefore, a minimum of 2 days of hypomania was used in the present invention to diagnose BD-II.

(b) Study Design

Eligible patients were given low-dose (less than 5 mg/day) add-on memantine (5 mg/day) after an initial screening, with open-label valproic acid (VPA) treatment (500 or 1000 mg/day or 50-100 µg/dl in plasma) which had begun when they joined the study. The severity of mood symptoms was assessed by using the Hamilton Depression Rating Scale (HDRS) and the Young Mania Rating Scale (YMRS). Only patients with moderate mood symptoms (HDRS≥18 or YMRS≥14) were recruited. The exact amount of alcohol used by each patient was assessed by using the Chinese version of the Modified SADS-L. Symptom severity and alcohol use were assessed at baseline, and treatment responses were measured on day 7 of weeks 1, 2, 4, 8, and 12. Concomitant benzodiazepine medications (lorazepam<8 mg and chlordiazepoxide<240 mg) were used for nighttime sedation and withdrawal symptoms during the study. Up to 20 mg/day of fluoxetine was permitted for associated depressive symptoms, and 1-3 mg of risperidone was used for hypomanic symptoms.

Ten milliliters of whole blood was withdrawn from the antecubital vein of each patient when clinical severity was assessed: at baseline, and on day 7 of weeks 1, 2, 4, 8, and 12. Plasma, which was isolated from the whole blood after it had been centrifuged at 3000 g for 15 min at 4° C., was immediately stored at −80° C. The enzyme-linked immunosorbent assay was used to quantify the cytokine levels by ELISA reader (SpectraMax® M2e, Molecular Devices, USA). Sample processing and data analysis were done according to the manufacturer's instructions. The immunological parameters—plasma TNF-α, CRP, TGF-β1, IL-8, IL-10, and BDNF—were analyzed.

(c) Statistical Analysis

The demographic and clinical characteristics of the patients—baseline and endpoint YMRS and HDRS scores, alcohol use, and cytokine levels—were presented as means±standard deviation (SD).

The intent to-treat (ITT) analysis set included all patients who had taken at least one dose of the studied drug, and had undergone one baseline assessment and at least one post-baseline assessment. All outcome variables—HDRS, YMRS, cytokine levels, plasma BDNF levels, and metabolic parameters—in the ITT set were analyzed. Missing data were filled in by using the last observation carried forward (LOCF) method.

The overall within-group changes of each outcome over 12 weeks were analyzed by using generalized estimating equations (GEEs). The present invention ran 10 models and each outcome was deemed as a dependent variable. In each model, treatment duration, gender, and age were considered as independent variables. The covariance structure used was the autoregressive (AR [1]) model. The significance of change of each outcome over 12-week follow-up was represented by the variable "treatment duration." Linear regression analysis was used to analyze correlations between changes in alcohol use and changes in cytokine and BDNF levels in 12 weeks. Changes in alcohol use were dependent variables, and changes in HDRS and YMRS scores, and in plasma cytokine and BDNF levels (controlled for gender, age, and baseline clinical severity) were independent variables. SPSS 22.0 for Windows was used for all statistical computations. Significance was set at $p<0.05$.

Results:

The present invention initially screened 99 patients: 39 were excluded because they did not meet the criteria and 15 refused to participate. Forty-five BD-II patients with comorbid alcohol dependence were treated with low-dose (less than 5 mg/day) memantine for 12 weeks. Twenty-six (57.8%) of them completed the 12-week follow-up, and 19 (49.6%) dropped out: 17 refused follow-up, and 2 travelled abroad.

Demographic and clinical characteristics of the patients at baseline (45 patients) and endpoint (26 patients) comprising HDRS and YMRS scores, alcohol use, cytokine and BDNF levels were presented in Table 1.

TABLE 1

Demographic and clinical characteristics of the patients at baseline and endpoint

| Variable | Baseline (n = 45) | | Endpoint (n = 26) | |
|---|---|---|---|---|
| | Mean | SD | Mean | SD |
| HDRS | 14.4 | 3.9 | 9.4 | 3.2 |
| YMRS | 13.8 | 2.5 | 9.4 | 2.9 |
| Alcohol use (unit) | 73.9 | 58.3 | 11.8 | 38.8 |
| TNF-α | 2.64 | 2.07 | 2.66 | 1.85 |
| CRP | 2960.48 | 1983.52 | 2382.29 | 1666.26 |
| BDNF | 16196.64 | 10699.20 | 18910.46 | 11743.63 |
| IL-8 | 17.64 | 37.93 | 10.22 | 25.60 |
| TGF-β1 | 30884.32 | 18941.671 | 27653.85 | 17175.710 |
| IL-10 | 2.09 | 2.080 | 1.92 | 2.333 |

SD: standard deviation; HDRS: Hamilton Depression Rating Scale; YMRS: Young Mania Rating Scale; TNF-α: tumor necrosis factor α; CRP: C-reactive protein; BDNF: brain-derived neurotrophic factor; IL-8: Interleukin-8; TGF-β1: Transforming growth factor-β1; IL-10: Interleukin-10.

After 12 weeks of treatment, the within-group mean value of clinical severity (HDRS and YMRS scores) ($p<0.001$), alcohol use ($p<0.001$), CRP ($p=0.012$), and IL-8 levels ($p=0.021$) decreased significantly (Table 2). BDNF levels were significantly ($p=0.018$) higher (Table 2).

TABLE 2

Changes in clinical severity, alcohol use, and cytokine levels over 12 weeks of treatment

| Variable | Baseline | Endpoint |
| --- | --- | --- |
| HDRS | −5.0 | <0.001** |
| YMRS | −4.4 | <0.001** |
| Alcohol use | −61.99 | <0.001** |
| TNF-α | 0.04 | 0.89 |
| CRP | −610.08 | 0.012* |
| BDNF | 3096.04 | 0.018* |
| IL-8 | −7.86 | 0.021* |
| TGF-β1 | −3586.37 | 0.080 |
| IL-10 | −0.182 | 0.605 |

HDRS: Hamilton Depression Rating Scale; YMRS: Young Mania Rating Scale; TNF-α: tumor necrosis factor α; CRP: C-reactive protein; BDNF: brain-derived neurotrophic factor; IL-8: Interleukin-8; TGF-β1: Transforming growth factor-β1; IL-10: Interleukin-10.

No significant correlation was found between changes in alcohol use or HDRS and YMRS scores. The correlation between changes in alcohol use and in TGF-β1 levels, however, was significant (B=0.003, p=0.019) (Table 3 and FIG. 1).

TABLE 3

Relationship between changes in alcohol use vs. changes in cytokine levels

| Variable | Baseline | Endpoint |
| --- | --- | --- |
| HDRS | −0.28 | 0.93 |
| YMRS | 2.15 | 0.54 |
| TNF-α[a] | −3.71 | 0.56 |
| CRP[a] | 0.003 | 0.671 |
| BDNF[a] | 0.001 | 0.402 |
| IL-8[a] | 0.532 | 0.329 |
| TGF-β1[a] | 0.003 | 0.019* |
| IL-10[a] | 4.539 | 0.508 |

HDRS: Hamilton Depression Rating Scale; YMRS: Young Mania Rating Scale; TNF-α: tumor necrosis factor α; CRP: C-reactive protein; BDNF: brain-derived neurotrophic factor; IL-8: Interleukin-8; TGF-β1: Transforming growth factor-β1; IL-10: Interleukin-10.
Controlled for age and gender.
[a]Controlled for age, gender, and baseline HDRS and YMRS scores.

Overall, 15 patients (33.3%) stopped drinking during the first week of memantine treatment. After 12 weeks of treatment, all of the patients greatly reduced their alcohol use>50%, and 22 (22/26) patients (84.6%) reduced their alcohol use to 0 unit after 12 weeks of this treatment.

CONCLUSION

The most important finding of the present invention was that low-dose (less than 5 mg/day) add-on memantine treatment significantly attenuated clinical severity, reduced alcohol use and plasma cytokine levels, and increased BDNF levels. The present invention also found a significant correlation between reductions in alcohol use and in plasma TGF-β1 levels. The results of the present invention showed that low-dose add-on memantine for BD-II patients with comorbid alcohol dependence was associated with reduced alcohol use, attenuated clinical symptoms, and downregulated cytokine levels.

The present invention found no correlation between attenuated clinical severity and reduced alcohol use, which demonstrated that the changes in alcohol use was not associated with BD-II treatment. One clinical study reported that pretreatment with memantine might reduce craving for alcohol. An animal study also reported that, in post-dependent (PD) rats, a memantine injection (25 mg/kg) reduced alcohol drinking during acute withdrawal, but did not reduce relapses of alcohol dependence after protracted abstinence. In a pilot double-blind trial, up to 40 mg/day of memantine was used, alcohol use was not significantly reduced as compared to placebo. However, in the present invention only 5 mg/day of memantine was given to the patients, the patients' plasma memantine concentrations were about 10-50 ng/ml (0.05-0.2 μM). This ultralow level of plasma memantine was insufficient to block NMDA receptors (50% inhibition concentration [$IC_{50}$] of memantine=2-3 μM).

The inventors previously reported an alternative mechanism of memantine: providing an anti-inflammatory effect by reducing the activity of microglia and increasing the release of neurotrophic factors by astroglia, which were mechanistically remote from an NMDA receptor. Therefore, the present invention found a significant correlation between reduced alcohol use and reduced plasma TGF-β1 levels. The finding of a positive correlation between reduced alcohol use and reduced TGF-β1 levels in the present invention demonstrated that reduction of alcohol use reduces alcohol-induced liver fibrosis and hepatocyte apoptosis. The present invention demonstrated that the anti-inflammatory and/or neurotrophic effect provided by the low dose add-on memantine was involved in reducing plasma TGF-β1 levels, which, in turn, might contribute to reduction of alcohol use. Therefore, the reduced alcohol use in the present invention was the result of memantine's anti-inflammatory and/or neurotrophic effect, not the function of an NMDA-receptor antagonist.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method for treating bipolar disorder comorbid with alcohol dependence or alcohol abuse in a subject, comprising administering to the subject a composition comprising an effective amount of memantine, wherein the effective amount of memantine is 2-4.7 mg/day for at least two weeks to provide anti-inflammatory response and neurotropic effect.

2. The method of claim 1, wherein the bipolar disorder is bipolar II disorder.

3. The method of claim 1, wherein the anti-inflammatory response and the neurotropic effect comprise reducing the plasma level of TGF-β1 in the subject.

* * * * *